March 14, 1933. A. F. J. BAUR Plant Pat. 56
CARNATION
Filed Nov. 17, 1932
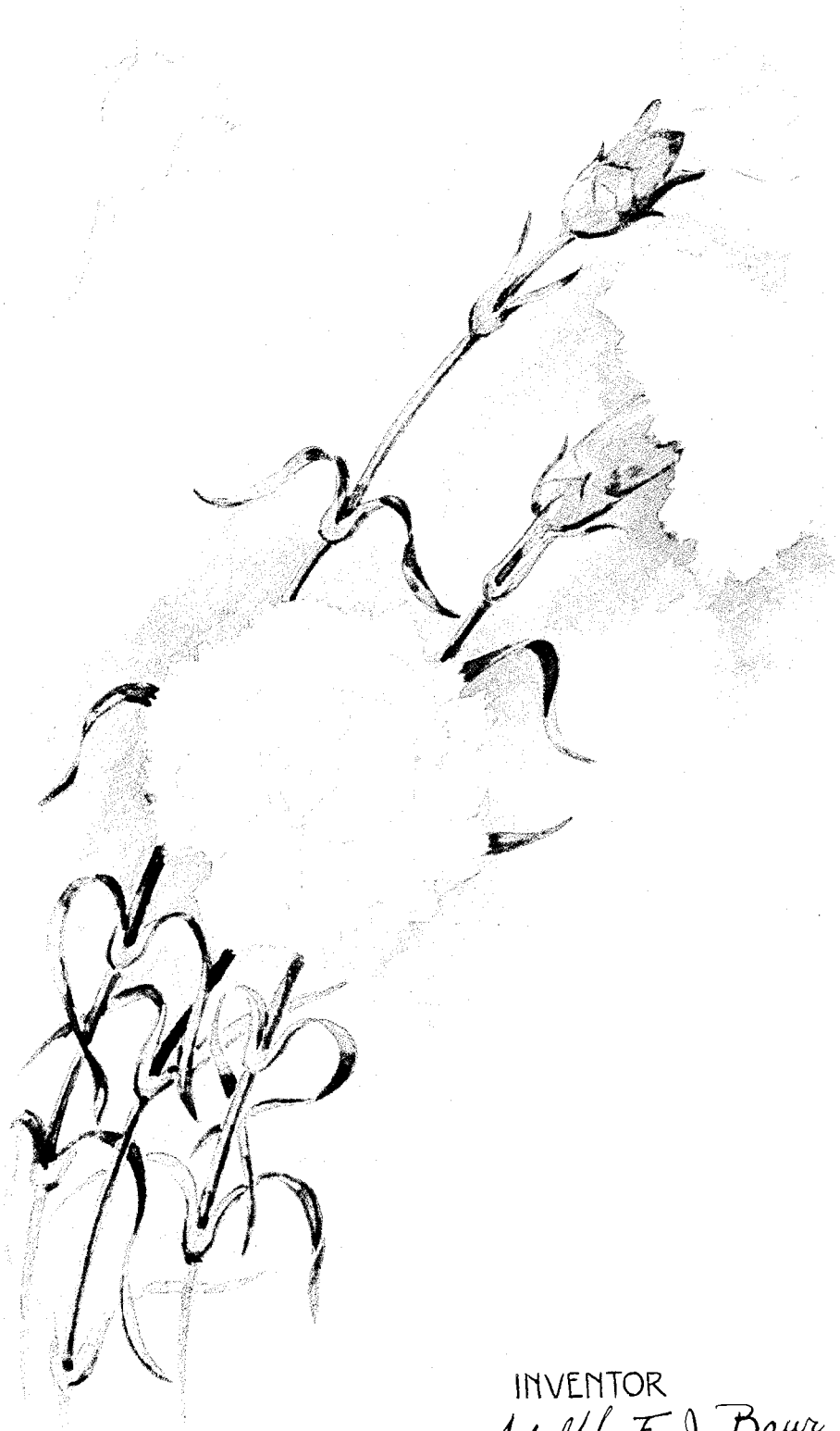
INVENTOR
Adolphe F. J. Baur
By Orville M. Kile
PLANT PATENT AGENT Patented Mar. 14, 1933

Plant Pat. 56

UNITED STATES PATENT OFFICE

ADOLPHE F. J. BAUR, OF INDIANAPOLIS, INDIANA, ASSIGNOR TO BAUR-STEINKAMP & COMPANY, INC., OF INDIANAPOLIS, INDIANA

CARNATION

Application filed November 17, 1932. Serial No. 643,087.

My invention relates to improvements in fragrant, pink, carnations of the type ordinarily known as perpetual blooming or greenhouse forcing carnations. The object of my improvement is to provide a carnation in the light pink class having essentially all the desirable commercial qualities of the extensively grown variety Pink Abundance in the medium pink class.

My new variety is a sport of Pink Abundance and was discovered by me during or about the month of April 1929. Being an extensive grower of Pink Abundance, I have made it a part of my business to search out, observe and study any sport developments among my growing plants. Any apparent new varieties thus discovered or developed are carefully tested to determine more definitely their superior qualities and to make certain that these qualities will reproduce.

The accompanying illustration indicates the characteristic features of this new variety but it must be understood that the artist's brush is incapable of fully portraying the color effects, there being a tendency to use deeper color tones in the shaded areas as a means of emphasizing the petal outlines. In the natural daylight and to the casual observer the coloring appears more uniformly distributed over the flower than is the case in the heavily shaded paintings submitted herewith. The coloring of the main part of the individual petal shown in the upper left portion of the plate is substantially correct and accurate as to color tone but in the shaded areas shows this same tendency of the artist to deepen the color tone as a means of expressing shadows and bringing out sharper definition of detail.

The following is a detailed description of this new variety of carnation:

*Growth habits.*—Practically identical with those of Pink Abundance. The plants produce a fine open growth, with long slender stems and narrow leaves. It makes no surplus "grassy" growth and comes into bloom quickly and blooms freely and continuously throughout the season. It is a heavy producer, giving about thirty per cent more blooms than Enchantress Supreme, another well known light pink variety. It shows no tendency toward stem rot, such as characterizes another light pink variety recently introduced, namely Jane Sutherland.

*Flowers.*—May be popularly described as shell pink or light pink, but according to Ridgeway's Color Standards and Nomenclature the main part of the petal classifies as "Venetian pink" (Plate XIII), while portions of the petal near and at the outer edges approximate "Jasper pink" (Plate XIII).

A few petals on most specimens are slightly edged or flecked with bright pink. The under sides of the petals are of a lighter shade than the upper sides. The flower is medium in size, about 2½ inches across, dense and compact, having about 37 petals during the month of October. Petal edges irregularly serrated. Two white styles arise from the top of the ovary and there are 12 to 15 white stamens mounted by small white anthers. In general, the size, shape, and petal arrangement of this variety is identical with that of Pink Abundance from which it sported. It has a distinct cinnamon odor.

*Calyx.*—The calyx is relatively long and slender being about 1⅛ inches long and ⅝ to ¾ inches wide at top. The calyx is 5 lipped, not deeply divided nor subject to bursting, construction in this respect being superior to Enchantress Supreme. Six bracts are found at the base of the calyx.

*Stem and foliage.*—Stems are of moderate length, slender, smooth, bluish green in color and having but a slight gray bloom. The leaves are of the same blue green color as the stems, with yellowish shades at the points of attachment to the stem. Leaves are rather short and narrow, those at the third node below the blossom measuring 1¾ inches to 2 inches in length.

I claim:

The variety of carnation herewith described and shown, characterized particularly by its flowers of light pink color, medium size and large yield, also by its freedom from disease and by other superior growing and blooming habits.

In testimony whereof I affix my signature.

ADOLPHE F. J. BAUR.